United States Patent
Johnson

(10) Patent No.: US 11,654,309 B2
(45) Date of Patent: May 23, 2023

(54) COWL NECK BARRIER GOWN WITH ATTACHMENTS

(71) Applicant: Debra Sharon Johnson, Canton, GA (US)

(72) Inventor: Debra Sharon Johnson, Canton, GA (US)

(*) Notice: Subject to any disclaimer, the term of this patent is extended or adjusted under 35 U.S.C. 154(b) by 328 days.

(21) Appl. No.: 17/030,379

(22) Filed: Sep. 24, 2020

(65) Prior Publication Data

US 2021/0008396 A1    Jan. 14, 2021

Related U.S. Application Data

(60) Continuation of application No. 16/020,884, filed on Jun. 27, 2018, now Pat. No. 10,905,904, and a (Continued)

(51) Int. Cl.
*A62B 17/00* (2006.01)
*A62B 18/02* (2006.01)
(Continued)

(52) U.S. Cl.
CPC ........ *A62B 17/006* (2013.01); *A41D 13/1218* (2013.01); *A41D 19/0041* (2013.01); (Continued)

(58) Field of Classification Search
CPC ............... A62B 17/0006; G01K 13/20; A41D 13/1218; A41D 19/0041; A41D 13/0005; A41D 13/1184; A41D 2200/20; A43B 1/0081; A43B 3/18; A43B 17/04; A43B 18/02; A43B 5/01; A43B 5/6803; A43B 2503/04; A43B 1503/06; A43B 2503/12; A43B 2503/40; A43B 2562/0271
See application file for complete search history.

(56) References Cited

U.S. PATENT DOCUMENTS

| | | | |
|---|---|---|---|
| 2011/0185482 A1* | 8/2011 | Godfrey | A41D 13/1161 2/455 |
| 2015/0174434 A1* | 6/2015 | Condon | A62B 17/005 2/457 |

(Continued)

*Primary Examiner* — Steven O Douglas
(74) *Attorney, Agent, or Firm* — Scott D. Smiley; Scott M. Garrett; The Concept Law Group, P.A.

(57) ABSTRACT

This invention offers a fully protective cowl neck garment with various fasteners designed to attach additional protective gear, such as gloves and shoe coverings. Additionally, a temperature sensor shield is located on the hat and protective mask. This allows the clients or patients the ability to see and to monitor the temperature of their caregivers. The caregiver's temperature is visible on the hat, as well as the face mask. This makes the caregivers accountable to their clients or patients, as well as their colleagues and coworkers. This invention eliminates the worry of contact with infectious diseases or dangerous liquids, by utilizing elastic manual ties and hook-and-loop fasteners to ensure the garment is secured fully on a user's body. Overall, this invention ensures medical professionals, firemen, emergency medical personnel, government workers, and so forth, are protected fully from contagious and infectious diseases, liquids, and so forth.

18 Claims, 4 Drawing Sheets

Related U.S. Application Data continuation of application No. 16/018,058, filed on Jun. 26, 2018, now Pat. No. 10,850,139, said application No. 16/020,884 is a division of application No. 14/990,790, filed on Jan. 8, 2016, now Pat. No. 10,039,941, said application No. 16/018,058 is a continuation of application No. 14/990,790, filed on Jan. 8, 2016, now Pat. No. 10,039,941.

(60) Provisional application No. 62/101,028, filed on Jan. 8, 2015.

(51) Int. Cl.
| | |
|---|---|
| *A41D 19/00* | (2006.01) |
| *A43B 3/18* | (2022.01) |
| *A62B 17/04* | (2006.01) |
| *A41D 13/12* | (2006.01) |
| *A43B 1/00* | (2006.01) |
| *G01K 13/20* | (2021.01) |
| *A61B 5/01* | (2006.01) |
| *A61B 5/00* | (2006.01) |
| *A41D 13/00* | (2006.01) |
| *A41D 13/11* | (2006.01) |

(52) U.S. Cl.
CPC .............. *A43B 1/0081* (2013.01); *A43B 3/18* (2013.01); *A62B 17/04* (2013.01); *A62B 18/02* (2013.01); *G01K 13/20* (2021.01); *A41D 13/0005* (2013.01); *A41D 13/1184* (2013.01); *A41D 2200/20* (2013.01); *A61B 5/01* (2013.01); *A61B 5/6803* (2013.01); *A61B 2503/04* (2013.01); *A61B 2503/06* (2013.01); *A61B 2503/12* (2013.01); *A61B 2503/40* (2013.01); *A61B 2562/0271* (2013.01)

(56) References Cited

U.S. PATENT DOCUMENTS

| | | | |
|---|---|---|---|
| 2016/0213959 A1* | 7/2016 | Barklow | A41D 13/1107 |
| 2017/0100613 A1* | 4/2017 | Chessari | A62B 17/04 |
| 2022/0039497 A1* | 2/2022 | Magdlen | A41D 13/1161 |
| 2022/0312868 A1* | 10/2022 | Holliday | A62B 7/10 |

* cited by examiner

COWL NECK BARRIER GOWN WITH ATTACHMENTS

STATEMENT OF RELATED APPLICATIONS

This application is a continuation of U.S. patent application Ser. No. 16/020,884 filed Jun. 27, 2018, which claims from U.S. patent application Ser. No. 14/990,790 filed Jan. 8, 2016, which claims from U.S. Provisional Patent Application No. 62/101,028 filed Jan. 8, 2015. This application also is a continuation of U.S. patent application Ser. No. 16/018,058 filed Jun. 26, 2018, which claims from U.S. patent application Ser. No. 14/990,790 filed Jan. 8, 2016, which claims from U.S. Provisional Patent Application No. 62/101,028 filed Jan. 8, 2015.

BACKGROUND OF THE INVENTION

Protective garments such as surgical and disposable gowns are well known. This is a time of great concern for the medical profession when treating infectious and contagious patients. The medical professionals typically wear protective suits and coverings to prevent contamination and disease transmission. These suits, while offering a great deal of protection, still may not be useable to protect all areas of the body. Contamination outside a designated area can result in serious consequences. Further, some people may be unable to fit into standard protective garments and may be left with baggy or ill-fitting clothing. Therefore, there is a need for a gown, pants, gloves, and shoe coverings that offer comfort and total protection.

Conventional disposable surgical gowns commonly are constructed from a nonwoven fabric. The gown body section is generally a singular piece of material or is composed of a number of panels of material attached together. An example of a single gown made using raglan-type sleeves, attached to a one-piece gown body, is the light weight gown (product code 90751) from Kimberly-Clark, Corp. of Neenah, Wis., U.S.A.

A drawback to the conventional gown is that the gowns tends to need extra protection in the front chest and torso area. These are the areas most susceptible to the various contaminates. There also is a problem with most gowns being too short for the larger professionals. I have been able to solve these problems by designing a longer gown that comes below the knees and that has attached to the front chest torso area, a plastic apron for extra protection. This is a fixed attachment making the apron easily accessible at all times. There also is a fixed mask made into the collar of the gown, making it easily accessible at all times while wearing the disposable gown.

There are several types of headpieces and devices available to add to the protection of the gown. Some devices provide a protective garment that facilitates protection of the neck and chest of an individual. There are other devices that provide isolation garments with footwear attachments. These devices, however, fail to provide a cowl neck garment with fasteners at the waist, shoulders, and the extremities for the attachment of accessories, such as gloves, shoe covers, and headpieces. This invention relates to a unique configuration for Personal Protective Equipment (hereinafter referred to as "PPE") that can be worn as layers closing tightly the areas of the wrist and/or upper arms and the ankles and/or legs. Certain drawbacks with conventional gowns can be addressed without sacrificing the gown and other PPE protective wear's nature or compromising any sterile fields.

BRIEF SUMMARY OF THE INVENTION

Objects and advantages of this invention will be set forth in part in the following description, or may be obvious from the description, or may be learned through practice of this invention. This invention relates particularly to a surgical gown, surgical pants, short- and boot-length shoe covers, short and long gloves, and attaching headpiece and mask. The gloves and shoe coverings are attached to the garments with hook-and-loop fasteners. The mask, shield, and hat have a thermometer made in or on them, allowing the garment user's temperature to be displayed clearly. The gown relates to a unique configuration for a protective garment. It has a closed front, an open back, and long sleeves finished with an elastomeric material. The closed front defines a cowl neck collar which extends high on the neck in the front, displaying a N95 or higher filtration mask attached to and/or made into the collar of the garment. The closed front also incorporates a section of barrier repellant material that extends from an upper chest region of the garment to a location above the bottom edge of the gown, which extends below the wearer's knees when the garment is donned. The sleeves have two rows of hook-and-loop fastening straps for a tight fitting and secure attachment of the gloves. The gloves are available in two lengths. One length should attach with hook-and-loop fastening straps at the wrist area. The second choice of gloves should attach with hook-and-loop fastening straps below the elbow area. The back of the gown has an attached hood that can be attached to the gown with sections of hook-and-loop fastening strips. It attaches on one side in the back and on one or more strips in the front and/or sides. The border region of the face of the hood is finished with elastomeric material or elastomeric finishing.

The pants have a waist band of elastomeric material and an attached belt and/or draw string belt for extra support. The bottom edge of the pant legs are finished with an elastomeric material. The pants have two rows of hook-and loop fastening straps for tight fittings and a more secure attachment that allows the shoe coverings to be either attached at the ankle with hook-and-loop fastening straps, or below the knee with hook-and-loop fastening straps.

The headpiece is part of this unique invention. It consists of a hat and shield. A mask can be attached to the shield or worn unattached under the shield. The hood can be worn under the shield or hung loose on the back for convenience.

The unique configuration of this invention provides significant benefits to the wearer. The hook- and-loop fastening attributes to the security of and tailored fit for each individual. Double or triple gloving is recommended when protecting the health care professionals from potentially harmful contaminants. An added benefit is the fact that once the outer gloves are removed, the wearer then can untie the back of the gown and disrobe without taking off the attached gloves. Then the pants can be taken off without detaching the attached shoe covers as well. The garments are turned inside out for a safe and effective removal process. The garment should be able to be taken off as one or two pieces. The pants and shoe covers come off as a single unit. The gloves and gown can come off as a single unit. Alternatively, the gown, gloves, pants, and shoe covers all can come off as a single unit. The headpiece can come off as an attachment or a single unit.

This equipment will come in various sizes and colors, ranging from extremely large sizes to sizes for children and babies. No one should be left out. Thus, it should be appreciated that the style and configuration of this invention is not a limiting factor. Regardless of the type of garment, it should be appreciated that PPE (Personal Protective Equipment) constructed in accordance with this invention is not limited to any particular types of materials. Conventional materials for making PPE are well known to those skilled in the art, and any such material may be used for PPE in accordance with this invention. Likewise, there are a number of elastomeric extensible materials used in the art that may serve adequately as the elastomeric material section for use in this invention. This invention is in no way intended only for human beings. The complete embodiment or portions of this invention can be extended to apply to pets and other animals. This serves to be a very unique and different invention.

BRIEF DESCRIPTION OF THE DRAWINGS

A full and enabling disclosure of this invention, including the best mode thereof, directed to one of ordinary skill in the art, is set forth more particularly in the remainder of the specification, which makes reference to the appended figures in which.

DETAILED DESCRIPTION OF PREFERRED EMBODIMENTS

Figure 1:
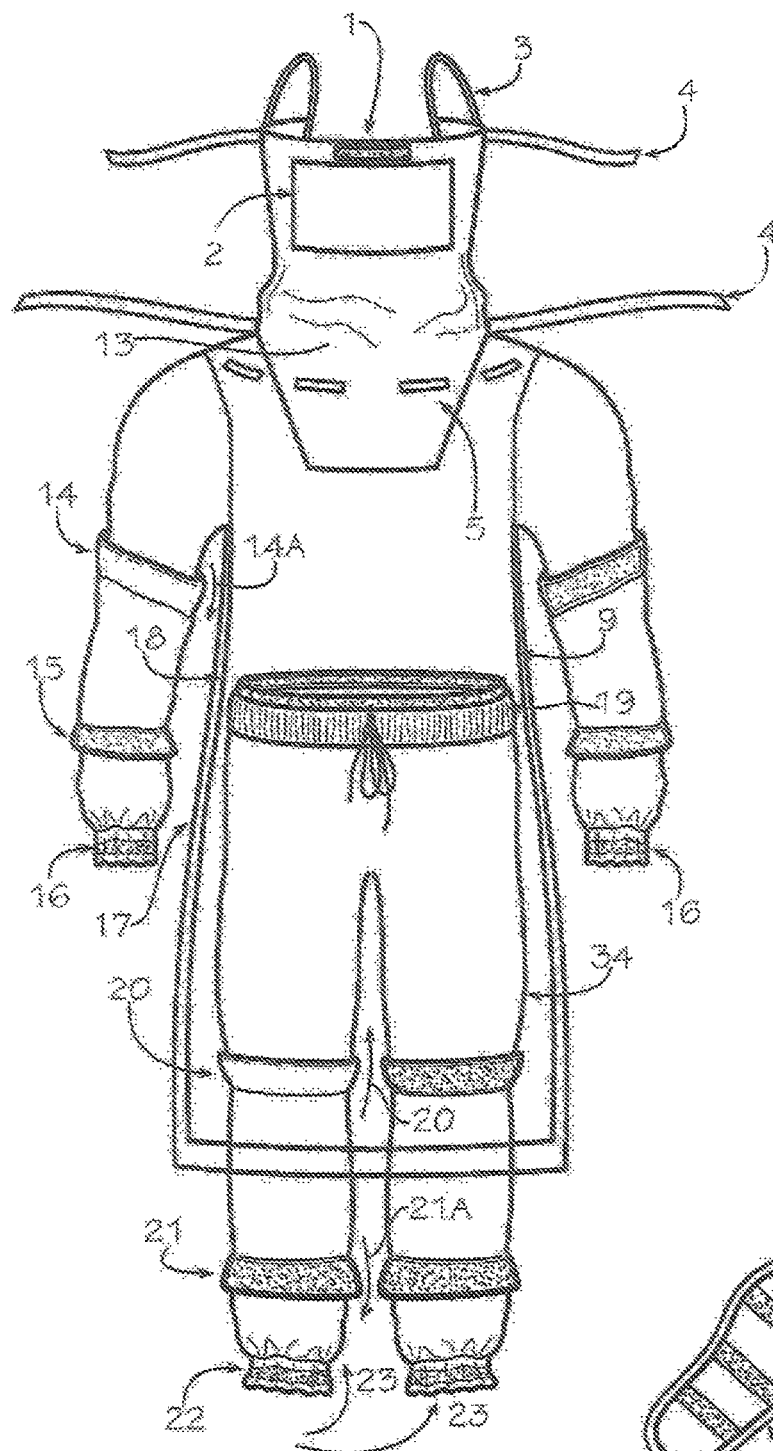
FIG. 1 is a front view of an embodiment of a protective garment and pants in accordance with this invention.
Figure 2:
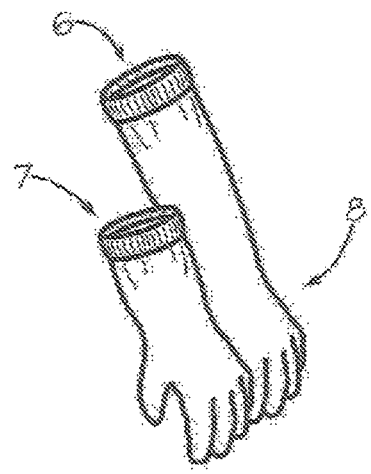
FIG. 2 is a front view of gloves attachment in accordance with this invention.
Figure 3:
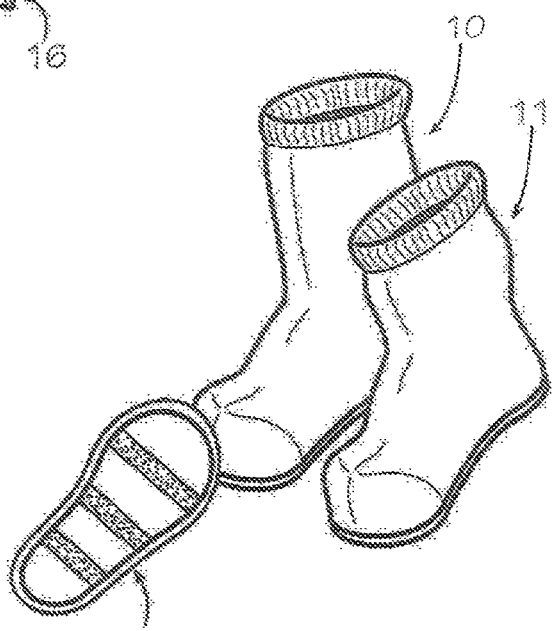
FIG. 3 is a side and bottom view of shoe attachments in accordance with this invention.

Reference now will be made in detail to one or more embodiments of this invention, examples of which are illustrated graphically in the drawings. Each example and embodiment is provided by way of explanation of this invention, and not meant as a limitation of the invention. For example, features illustrated or described as part of one embodiment may be utilized with another embodiment to yield still a further embodiment. It is intended that this invention include these and other modifications and variations.

As used herein, the term "garment" refers to protective garments and/or shields, including for example, but not limited to, surgical gowns, patient drapes, work suits, aprons, and so forth. As used herein, the term "liquid resistant" or "liquid repellant" refers to material having a hydrostatic head of at least about 25 centimeters as determined in accordance with the standard hydrostatic pressure test AATCCTM No. 1271977.

"Elastomeric" refers to a material or composite that can be extended or elongated by at least 25% of its relaxed length, and that will recover, upon release of the applied force, at least 10% of its elongation. It generally is preferred that the elastomeric material or composite be capable of being elongated by at least 100%, and recover at least 50% of its elongation. Thus, an elastomeric material is stretchable: "stretchable," "elastomeric," and "extensible" may be used interchangeably.

Figure 4:
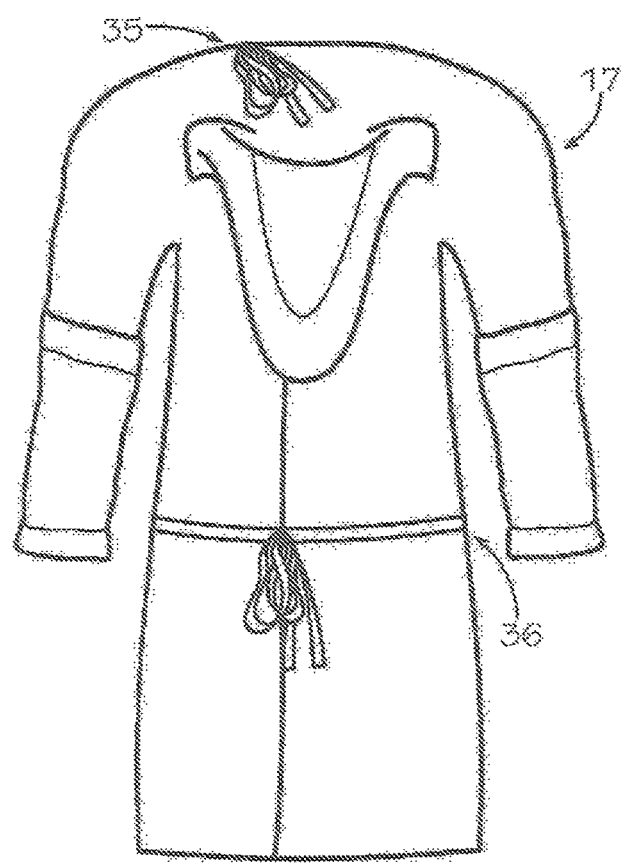
FIG. 4 is a back view of the embodiment of a protective garment in accordance with this invention.

"Elastic" or Elasticized" means that property of a material or composite by virtue of which it tends to recover towards its original size and shape after removal of a force causing a deformation. This invention relates to a unique configuration for a protective garment. The garment is illustrated and described herein as a disposable surgical gown and hazmat suit for illustrative purposes. It should be appreciated that a garment in accordance with this invention is not limited to a gown, coverall, robe, gloves, shoe covers, pants, headpieces, mask, thermometers, and so forth. A conventional gown is illustrated conceptually in FIG. 1. The gown includes a gown body 17 that is made from a generally non-elastomeric material and that has a closed front as illustrated in FIG. 1 and an open back as illustrated in FIG. 4. The back is "open" in that open sides provide access to the gown as illustrated again in FIG. 4 and FIGS. 11, 12, and 13. The gown body 17 may be formed from a single piece of material as illustrated in FIGS. 1, 4, 11, 12, 13, or may be defined by separate panels of material joined at the seams.

The sleeves may be of the same or different material of the gown body 17, and may be attached to the body at sleeve seams. Hook-and-loop fasteners 14 and 15 in FIG. 1 are located on the sleeves. There is a flap turned up on hook-and-loop fastener 14 on the upper sleeve in FIG. 1, allowing for an attachment of long glove 6, 8 in FIG. 1, and then the turning down of the flap 14A in FIG. 1. The lower hook-and-loop attachment 15 is for the attachment of the shorter glove 7 in FIG. 1, and then the turning down of the accompanying flap. The gloves 6 and 7 attach to the hook-and-loop fasteners 14 and 15, and then the flaps are positioned in a downward manner to help secure the gloves in place. Elastomeric cuffs 16 may be provided at the ends of the sleeves. Any conventional securing mechanism, such as strap or ties 35 and 36 in FIG. 4, may be provided with the closed front gown body 17 in FIG. 1 and/or open back of gown body 17 in FIG. 4 for securing the gown once donned. It should be appreciated that various configurations of gown are well known to those skilled in the art, and all such configurations are within the scope and spirit of this invention. The gown body 17 has a unique and unusual cowl neck collar 13 as illustrated in FIG. 1. The neck section of collar 13 extends up to the ears and is able to be held in place by the elastic material that goes around the ears 3 in FIG. 1. The cowl neck collar 13 of the body has a mask secured to or made into the front of the collar, making it available at all times while wearing this protective garment. The body portion of the mask 2 in FIG. 1 relates to a N95 greater or lesser filtration mask material. The border of the upper collar is secured with elastomeric type material 1 in FIG. 1. The elastic upper and lower ties 4 in FIG. 1 help to hold the mask snugly in place. The gown body 17, particularly its closed front, defines a hook-and-loop neck line 5 (in FIG. 1) that allows for the attachment of the hood 24 in FIG. 5.

Figure 5:
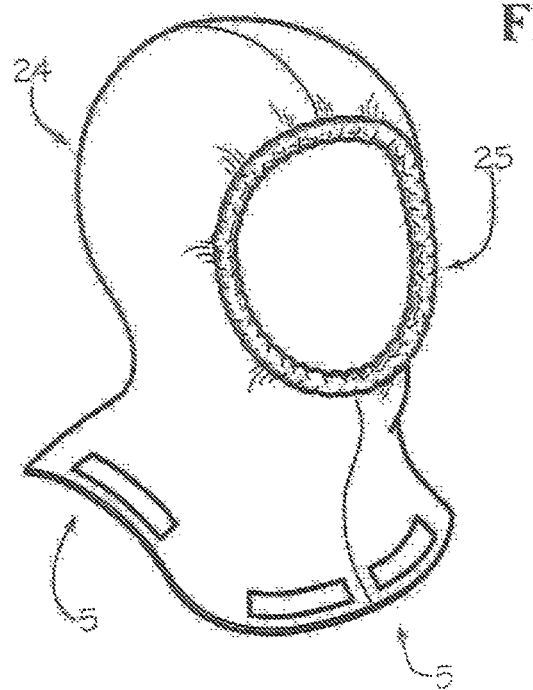
FIG. 5 is a front to side view of a hood of an embodiment of a protective garment in accordance with this invention.
Figure 6:
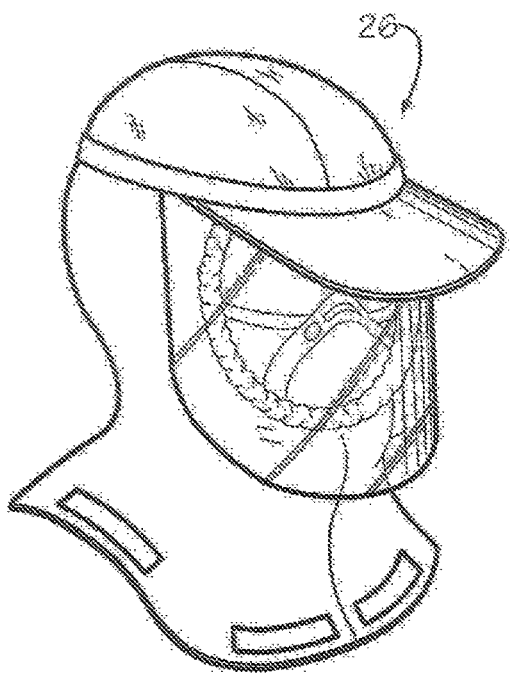
FIG. 6 is a front to side view of a hood of an embodiment of a protective garment with a visor in accordance with this invention.
Figure 12:
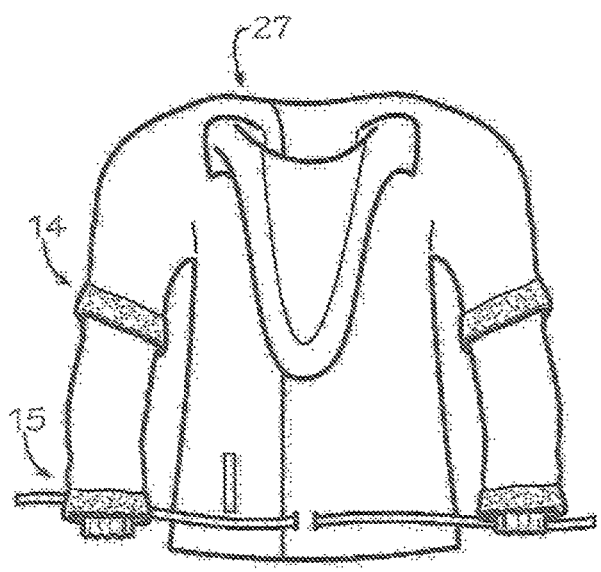
FIG. 12 is a back view of a protective garment displaying the hood attached in accordance with this invention.
Figure 13:
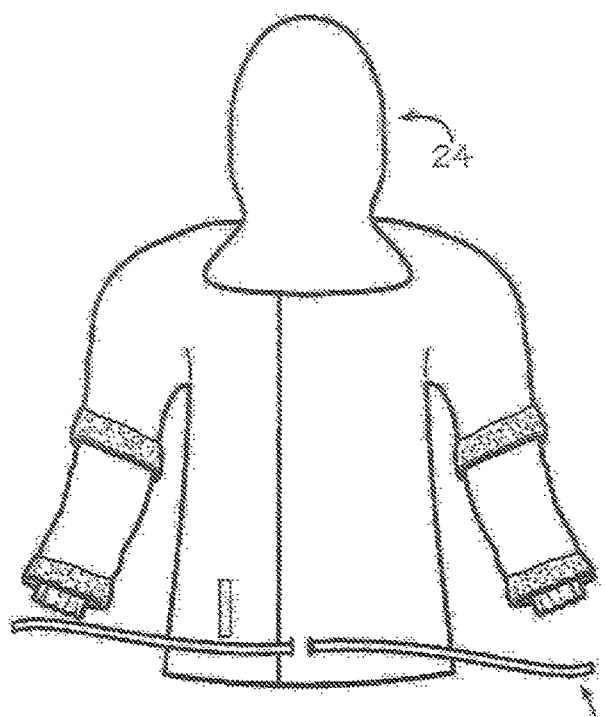
FIG. 13 is a back view of a protective garment displaying the hood fully assembled on the head in accordance with this invention.
Figure 14:
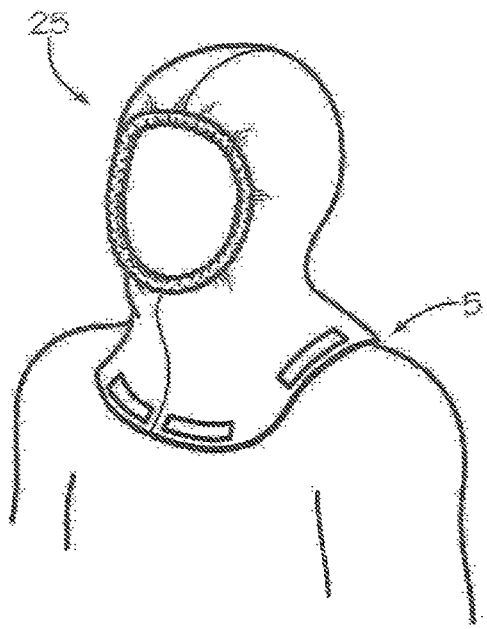
FIG. 14 is a side view of a protective garment in accordance with this invention.

The gown body 17 has a closed front, an upper chest region, a mid region, and a lower leg region extending down to the edge of the garment for a barrier type apron 9 as shown in FIG. 1. As defined in FIG. 1, the gown 17 has a length such that the edge extends below the wearer's knees. The apron front is made of a liquid repellant material that functions as a liquid resistant barrier material. The apron 9 extends from the upper chest region to the lower leg region. The embodiment of the apron 9 section may be incorporated into the closed front with a continuous seam around the periphery thereof. Such materials may be attached in many different ways. The illustration in FIG. 11 displays the back of the protective garment gown 27 having a hood that is attached on one side 37. FIG. 12 shows the back of the gown 27 having a hood firmly attached to the hook-and loop-fastener. FIG. 13 shows the hood pulled up to cover the head 24. The protective garment, gown, and hood section in FIG. 14 displays a front view of the hood 25 fully placed on the garment with hook-and-loop fasteners 5. The circumference of the face displays an elastic material 25 to help secure the hood and to protect the face area, as shown in FIGS. 5 and 14. FIG. 5 displays the hood 24 with an elastic type closing 25 for the hood and hook-and-loop fasteners 5 for the attachment of the hood to the protective gown. The illustration in FIG. 6 displays the hood with a protective visor 26 and shield in place for extra protection.

The gown body 17 includes a pair of disposable or surgical pants 34 (in FIG. 1) as part of the invention of protective garment. The pants 34 provides extra security by having a closed front, an elastic type material for a waist band 19, and a string tie. The pants 34 may be of the same or different material of the gown body 17. Defined on the legs of the pants are hook-and-loop fasteners 20 and 21, as illustrated in FIG. 1. There is a flap turned up on the upper leg that allows for an attachment of a shoe cover or boot 10 (FIG. 1) that extends to the calf or knee area of the leg. The flap is turned down to secure the attachment. Defined on the lower legs also is a loop-and-hook fastener 21 that allows for the attachment of a shorter boot 11 (FIG. 1) or shoe covering. Then the flap is turned down for a more secure attachment 21A (FIG. 1). The bottom of the shoe covers or boots display a type of traction. This can be made with strips or various materials 12 (FIG. 1). The top of the long and short boots or shoe covers display hook-and-loop-fasteners for a more secure fit. The pants legs of the protective garment are finished with an elastic type of material 22 at the hems 23 for a more secure fit. A suitable gown material is an appropriate chemical treatment to enhance liquid repellency and static decay.

Figure 7:
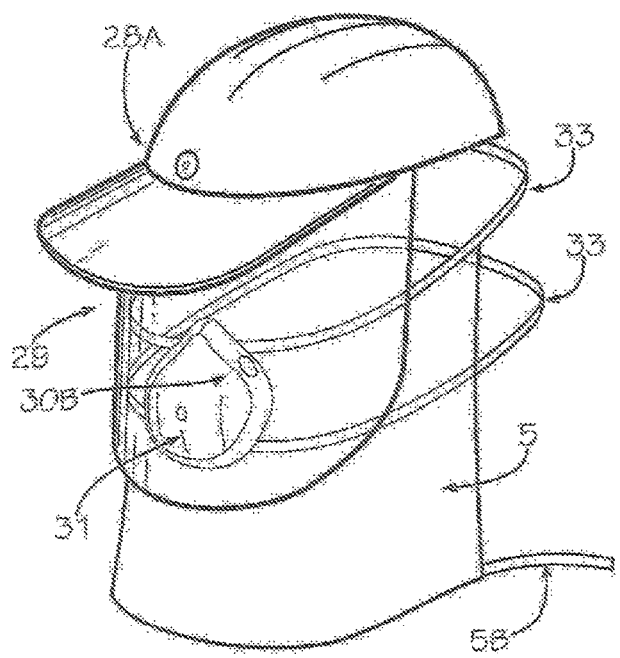
FIG. 7 is a front to side view of a protective garment, headpiece, and attachments in accordance with this invention.
Figure 8:
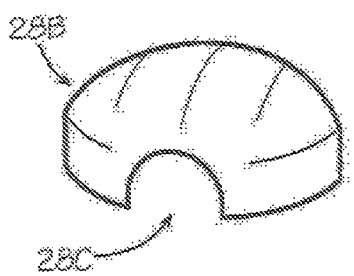
FIG. 8 is the back view of a hat of the protective garment in accordance with this invention.
Figure 10:
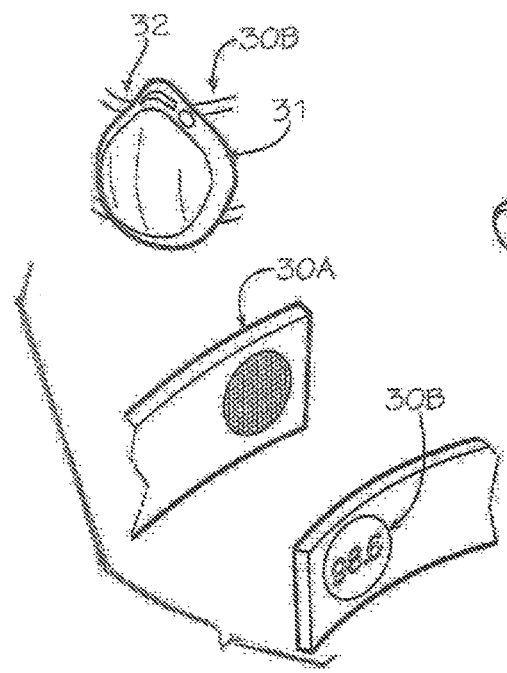
FIG. 10 is a view of protective attachments and thermometers in accordance with this invention.
Figure 9:
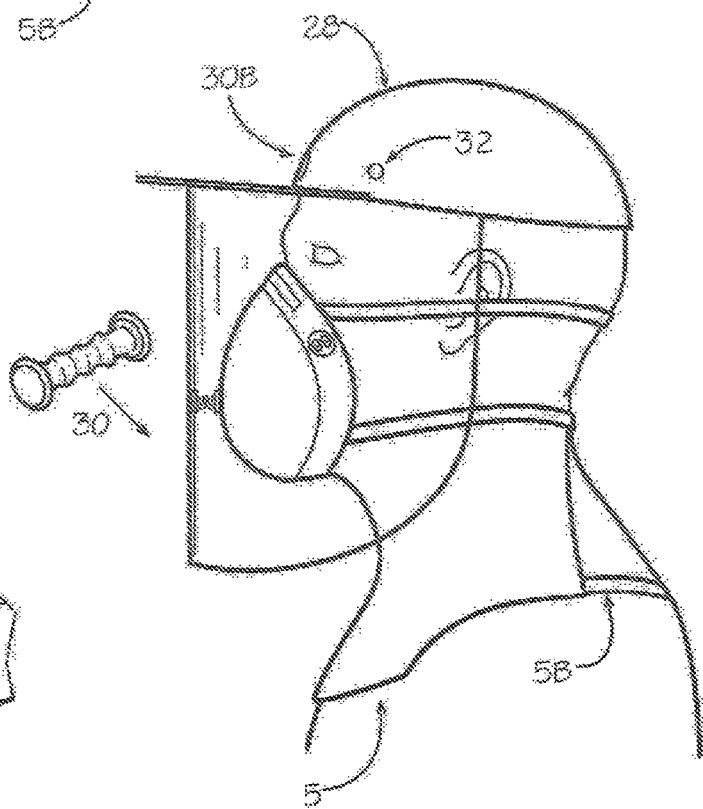
FIG. 9 is a side view of a protective garment, headpiece, and attachments in accordance with this invention.
Figure 11:
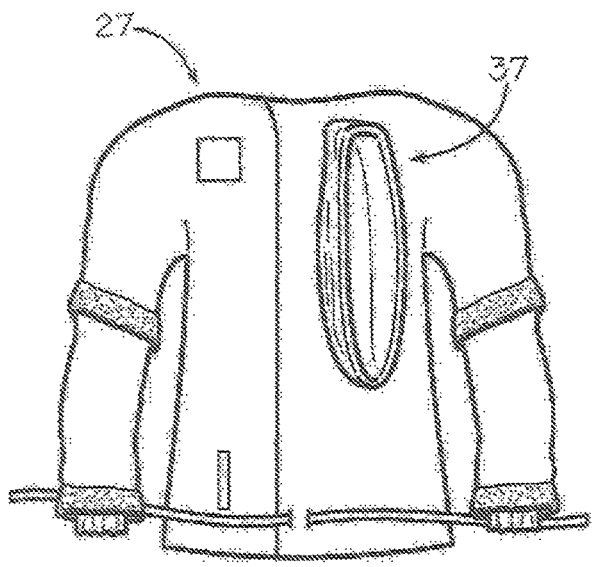
FIG. 11 is a back view of a protective garment displaying the hood unattached in accordance with this invention.

This invention relates in general to the field of face shields. More particularly, this invention's head gear relates to a disposable face shield. Face shields are used in a variety of industries to prevent splatter of liquids and materials onto a user's face. Face shields are used in the medical field for application during surgeries or various procedures. They prevent splatter of a patient's blood or other bodily fluids in the operator's face. It is most convenient to have disposable face shields made of inexpensive materials that can be replaced quickly. The following are non-limiting embodiments. One embodiment provides a face shield comprising a visor that is curved about multiple axes 29, as shown in FIG. 7, thereby providing for improved coverage and protection from patient-generated airborne droplets. As a result of this change from a cylindrical shape to a three dimensional shape with varying angles along multiple axes 29, the wearer's head supposedly is protected from the side as well as the bottom, significantly enhancing operational safety and user comfort. FIG. 7 shows a cap attached to the shield 28A for head coverage and protection. The cap 28 (FIG. 9) is shown in FIG. 8 at the backside 28B and allows for adjustments to be made 28C to accommodate the various head sizes and or shapes. FIGS. 7, 5, and 9 display a skirt that is attached to the upper portion of the protective gown by hook-and-loop fasteners 5. It can be worn with the attachments, or worn with a totally different gown for added protection. The illustrated protection garment is secured in place by a strap or tie at the bottom of the skirt SB in FIGS. 5 and 9. The protection garment equipment 31 in FIG. 7 also displays a face mask with a temperature thermometer 308, 30A (FIG. 10) made in or attached to it. This illustration shows a strip thermometer that is capable of detecting the temperature of the user. The temperature reads on one side 30A and is displayed on the other side 308 in LCD display. The illustration in 308 and 32 in FIG. 10 shows a possible button for activation of a sensor temperature monitor and a display of a LCD screen. The reading display screens can be either viewed by the public or hidden by a disposable covering, making the temperature reading private. There are many different ways to add a temperature thermometer to a mask, and this invention does not limit the ways. The face mask 31 in FIG. 7 also displays two elastic type straps 33 for a secure fit. This face mask attaches from the face shield to the mask with an accordion style device 30, or a similar attachment that is made of a suitable material. This allows for flexibility when wearing the mask and shield protective wear.

The protection garment and temperature thermometer are illustrated and described herein as part of the disposable shield, face mask, shield attachment, and hazmat suit. For illustrative purposes, it should be appreciated that a garment protection equipment in accordance with this invention is not limited to hats, face shields, face mask, straps, gear for the face, and so forth, revealing or having the attachment of a thermometer. Each explanation and illustration of this invention is not meant as a limitation of the invention and its attachments. An example is that features illustrated or described as part of one embodiment may be utilized with another embodiment to yield still another embodiment. It is intended that the present invention includes those and other modifications and variations. It should be appreciated by those skilled in the art that the system and method according to this invention have wide applications, and that the examples and embodiments set forth herein are merely exemplary. It is intended that this invention include such uses and embodiments as come within the scope and spirit of the appended claims.

What is claimed is:

1. A protective garment, comprising:
   a face mask comprising:
      a filtration component for filtering air for a user of the face mask during breathing;
      a cowl neck collar having a first end and a second end opposite the first end, and an elastomeric-type collar at the second end, the elastomeric-type collar configured as a closed looped border at the second end of the cowl neck collar or an open border at the second end of the cowl neck collar with each open end of the open border extending as an elastic tie on a first side of the cowl neck collar, the cowl neck collar also defined by a body portion between the first end and the second end on a second side of the cowl neck collar, the second side opposite the first side, the body portion for holding or situating the filtration component on the second side of the cowl neck collar, wherein the elastomeric-type collar is for holding the second side of the cowl neck collar up and in place along the user's face during use; and an elastic ear loop at the second end of the cowl neck collar configured to go around the user's ear, the elastic ear loop for holding the first side of the gaiter up and in place along the user's head and neck during use.

2. The protective garment as claimed in claim 1, additionally comprising a closed back open-front, or closed-front open-back, gown or apron for the user of the face mask for going over the first end of the cowl neck collar of the face mask without covering or obstructing the cowl neck collar of the face mask during use.

3. The protective garment as claimed in claim 1, additionally comprising a hood for the user of the face mask for going over the user's head and for going over the first side second end of the cowl neck collar of the face mask during use.

4. The protective garment as claimed in claim 3, wherein the hood for going over the user's head and the first side second end of the cowl neck collar also is for going over the first end of the cowl neck collar of the face mask during use.

5. The protective garment as claimed in claim 1, additionally comprising a flexible transparent face shield for the user of the face mask for covering the user's face and for covering the filtration component along the second side of the cowl neck collar of the face mask during use.

6. The protective garment as claimed in claim 1, wherein the face mask additionally comprises a thermometer defined by a reusable thermometer or thermometer sensor strip, the thermometer configured to come into contact with the user of the cowl neck collar of the face mask, the thermometer for reading the temperature of the user during use.

7. The protective garment as claimed in claim 1, wherein the filtration component is configured as a N95 mask, a surgical mask, a rigid or semi-rigid mask, a plastic mask, a shell mask, or a hollow chamber mask having a rear-facing opening and a rim wherein the rear-facing opening is pear shaped when viewed from the rear of the filtration component.

8. A protective garment, comprising:
a face mask comprising:
a filtration component for filtering air for a user of the face mask during breathing;
a cowl neck collar having a first end and a second end opposite the first end, and an elastomeric-type collar at the second end, the elastomeric-type collar configured as a closed looped border at the second end of the cowl neck collar or an open border at the second end of the cowl neck collar with each open end of the open border extending as an elastic tie on a first side of the cowl neck collar, the cowl neck collar also defined by a body portion between the first end and the second end on a second side of the cowl neck collar, the second side opposite the first side, the body portion for holding or situating the filtration component on the second side of the cowl neck collar, wherein the elastomeric-type collar is for holding the second side of the cowl neck collar up and in place along the user's face during use; and an elastic ear loop at the second end of the cowl neck collar configured to go around the user's ear, the elastic ear loop for holding the first side of the cowl neck collar up and in place along the user's head and neck during use; and a closed-front open-back gown or apron for the user of the face mask for going over the first end of the cowl neck collar of the face mask without covering or obstructing the cowl neck collar of the face mask during use.

9. The protective garment as claimed in claim 8, additionally comprising a hood for the user of the face mask for going over the user's head and for going over the first side second end of the cowl neck collar of the face mask during use, wherein the closed-front open-back gown or apron comprises a hook-and-loop neck line for attaching the hood to the gown or apron during use.

10. The protective garment as claimed in claim 9, wherein the hood for going over the user's head and the first side second end of the cowl neck collar also is for going over the first end of the cowl neck collar of the face mask during use.

11. The protective garment as claimed in claim 8, additionally comprising a flexible transparent face shield for the user of the face mask for covering the user's face and for covering the filtration component along the second side of the cowl neck collar of the face mask during use.

12. The protective garment as claimed in claim 8, wherein the face mask additionally comprises a thermometer defined by a reusable thermometer or thermometer sensor strip, the thermometer configured to come into contact with the user of the cowl neck collar of the face mask, the thermometer for reading the temperature of the user during use.

13. The protective garment as claimed in claim 8, wherein the filtration component is configured as a N95 mask, a surgical mask, a rigid or semi-rigid mask, a plastic mask, a shell mask, or a hollow chamber mask having a rear-facing opening and a rim wherein the rear-facing opening is pear shaped when viewed from the rear of the filtration component.

14. A protective garment, comprising:
a face mask comprising:
a filtration component for filtering air for a user of the face mask during breathing;
a cowl neck collar having a first end and a second end opposite the first end, and an elastomeric-type collar at the second end, the elastomeric-type collar configured as a closed looped border at the second end of the cowl neck collar or an open border at the second end of the cowl neck collar with each open end of the open border extending as an elastic tie on a first side of the cowl neck collar, the cowl neck collar also defined by a body portion between the first end and the second end on a second side of the cowl neck collar, the second side opposite the first side, the body portion for holding or situating the filtration component on the second side of the cowl neck collar, wherein the elastomeric-type collar is for holding the second side of the cowl neck collar up and in place along the user's face during use; and an elastic ear loop at the second end of the cowl neck collar configured to go around the user's ear, the elastic ear loop for holding the first side of the cowl neck collar up and in place along the user's head and neck during use;

a closed-front open-back gown or apron for the user of the face mask for going over the first end of the cowl neck collar of the face mask without covering or obstructing the cowl neck collar of the face mask during use; and a hood for the user of the face mask for going over the user's head and for going over the first side second end of the cowl neck collar of the face mask during use;

wherein the closed-front open-back gown or apron also comprises a hook-and-loop neck line for attaching the hood to the gown or apron during use.

15. The protective garment as claimed in claim 14, wherein the hood for going over the user's head and the first side second end of the cowl neck collar also is for going over the first end of the neck collar of the face mask during use.

16. The protective garment as claimed in claim 14, additionally comprising a flexible transparent face shield for the user of the face mask for covering the user's face and for covering the filtration component along the second side of the cowl neck collar of the face mask during use.

17. The protective garment as claimed in claim 14, wherein the face mask additionally comprises a thermometer defined by a reusable thermometer or thermometer sensor strip, the thermometer configured to come into contact with the user of the cowl neck collar of the face mask, the thermometer for reading the temperature of the user during use.

18. The protective garment as claimed in claim 14, wherein the filtration component is configured as a N95 mask, a surgical mask, a rigid or semi-rigid mask, a plastic mask, a shell mask, or a hollow chamber mask having a rear-facing opening and a rim wherein the rear-facing opening is pear shaped when viewed from the rear of the filtration component.

\* \* \* \* \*